US00PP20466P2

(12) United States Plant Patent
Hanes

(10) Patent No.: US PP20,466 P2
(45) Date of Patent: Nov. 10, 2009

(54) ***PELARGONIUM* PLANT NAMED 'COPE SCARFIR'**

(50) Latin Name: *Pelargonium Interspecific*
Varietal Denomination: Cope Scarfir

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,089

(22) Filed: Nov. 6, 2008

(51) Int. Cl.
*A01H 5/00* (2006.01)

(52) U.S. Cl. ..... Plt./330

(58) Field of Classification Search ..... Plt./330
See application file for complete search history.

*Primary Examiner*—Annette H Para
(74) *Attorney, Agent, or Firm*—S. Matthew Edwards

(57) ABSTRACT

A new *Pelargonium* plant named 'Cope Scarfir,' particularly distinguished by the dark scarlet-red flower color, large flower size, novel lateral plant habit, zonal like branching and foliage, and good garden performance growing well in both sun and slight shade.

1 Drawing Sheet

Latin name of the genus and species of the plant claimed: *Pelargonium Interspecific.*

Varietal denomination: 'Cope Scarfir'.

BACKGROUND OF THE NEW PLANT

The present invention comprises a new *Pelargonium*, botanically known as *Pelargonium Interspecific* and hereinafter referred to by the variety name 'Cope Scarfir.'

'Cope Scarfir' is a product of a planned breeding program. The new cultivar has scarlet-red flowers, large flower size, novel lateral plant habit, zonal like branching and foliage, and good garden performance growing well both sun and slight shade.

'Cope Scarfir' originated from a hybridization in a controlled breeding program in Gilroy, Calif. USA. The female parent was an unpatented *interspecific* hybrid seedling identified as '10136-1' with dark red color. '10136-1' has fewer petals and a smaller and more open plant habit than 'Cope Scarfir.'

The male parent of 'Cope Scarfir' was an unpatented *interspecific* hybrid seedling identified as '10241 - 1' with a burgundy-red color. '10241 - 1' has fewer petals, less vigor, smaller and more open plant habit than 'Cope Scarfir.'

'Cope Scarfir' was selected as one flowering plant within the progeny of the stated cross in 2006 in a controlled environment in Gilroy, Calif. USA.

The first act of asexual reproduction of 'Cope Scarfir' was accomplished when vegetative cuttings taken from the initial selection in the May 2006. The pollination took place in October 2005 and the seed sowing in March 2006, all in a controlled environment in Gilroy, Calif. USA Horticultural examination of plants grown from cuttings of the plant initiated in May 2006 in Gilroy, Calif. USA, and continuing thereafter, has demonstrated that the combination of characteristics as herein disclosed for 'Cope Scarfir' are firmly fixed and are retained through successive generations of asexual reproduction.

'Cope Scarfir' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cope Scarfir' has not been made publicly available more than one year prior to the filing of this application.

DESCRIPTION OF THE DRAWINGS

The accompanying photographic drawings show typical flower and foliage characteristics of 'Cope Scarfir' with colors being as true as possible with an illustration of this type. The photographic drawing shows 3 potted plants of the new variety, one of which is in flower and a close-up of the flowers. Both of the photographs were taken in April 2008 in Gilroy, Calif. USA. All plants were grown in Gilroy, Calif. USA and were approximately 4 months old.

DETAILED BOTANICAL DESCRIPTION

The measurements were taken in Salinas, Calif. USA in July 2008 on plants that were growing in one gallon pots. Culture of these plants started in a greenhouse in mid-spring 2008. They were transferred to the outdoors in mid June 2008 under semi-shade. The plants were approximately 4 months old Color chart used: Royal Horticultural Society Colour Chart (R.H.S.) 2001

BRIEF SUMMARY OF INVENTION

The following observations, measurements, and comparisons describe plants grown outside in Salinas, Calif. USA. The following traits have been repeatedly observed and are determined to be basic characteristics of the new variety. The combination of these characteristics distinguishes this *Pelargonium* as a new and distinct variety.

TABLE I

DIFFERENCES BETWEEN THE NEW VARIETY 'COPE SCARFIR' AND A SIMILAR VARIETY

| | 'Cope Scarfir' | 'Amri Dered' (U.S. Plant Pat. No. 17,236) |
|---|---|---|
| Flower color/size | Darker scarlet red/larger | Lighter scarlet red/smaller |
| Quantity of petals | Fewer | More |

TABLE I-continued

DIFFERENCES BETWEEN THE NEW VARIETY 'COPE SCARFIR' AND A SIMILAR VARIETY

| | 'Cope Scarfir' | 'Amri Dered' (U.S. Plant Pat. No. 17,236) |
|---|---|---|
| Floriferiousness | More flowers | Fewer flowers |
| Foliage color/size | Little darker/smaller | Little lighter/larger |
| Pedicel length | Longer | Shorter |

Plant:

*Form, growth and habit.*—Upright, outwardly spreading and rounded growth habit. Vigorous, well branched and grows well in sun or semi-shade.

*Plant height.*—16–21 cm.

*Plant height (inflorescence included).*—25–30 cm.

*Plant width.*—40–45 cm.

Foliage:

*Arrangement.*—Alternate, simple.

*Immature, leaf color, upper surface.*—RHS 137A but a little lighter.

*Lower surface.*—RHS 137C.

*Mature, leaf color, upper surface.*—RHS 137A.

*Lower surface.*—RHS 137C.

*Length.*—9.5–10.5 cm.

*Width.*—5.6–6.3 cm.

*Shape.*—Orbicular.

*Base shape.*—Reniform.

*Apex shape.*—Rounded.

*Margin.*—Irregularly crenate.

*Texture.*—Pilose; hirsute.

*Color of zone.*—None.

*Color of veins, upper surface.*—RHS 144A to almost indistinct.

*Color of veins, lower surface.*—RHS 144A.

*Petioles color.*—RHS 146A.

*Petioles length.*—8–10 cm.

*Diameter of petiole.*—0.3–0.4 cm.

*Texture.*—Pilose; hirsute; glandular hairs.

Stem:

*Color of stem.*—RHS 144A.

*Length of stem.*—16–20 cm.

*Diameter.*—0.8–0.9 cm.

*Length of internodes.*—1–1.5 cm.

*Texture.*—Pilose; hirsute; few glandular hairs.

Inflorescence:

*Type.*—An umbel composed of 18–23 flowers and buds.

*Umbel diameter.*—8.5–9.5 cm.

*Umbel depth.*—6.0–6.5 cm.

*Color of peduncle.*—RHS 144A but a little darker.

*Length of peduncle.*—12–16 cm.

*Peduncle diameter.*—0.3 –0.35.

*Texture.*—Pilose; hirsute; few glandular hairs.

*Color of pedicel.*—RHS 178A with RHS 178B basally.

*Length of pedicel.*—2.5–3.0 cm.

*Diameter of pedicel.*—0.15 cm.

*Texture.*—Slightly pilose; many glandular hairs.

Corolla:

*Form.*—Polypetalous, overlapping but some gaps between upper and lower petals.

*Number of petals.*—5–6.

*Width of flower.*—4.9–5.4 cm.

*Color upper petals, upper surface.*—Closest to RHS 45A but more a little more scarlet.

*Color upper petals, lower surface.*—RHS 50A.

*Length of upper petals.*—2.6–2.8 cm.

*Width of upper petals.*—1.9–2.1 cm.

*Color lower petals, upper surface.*—Closest to RHS 45B.

*Color lower petals, lower surface.*—RHS 50A.

*Length of lower petals.*—2.4–2.6 cm.

*Width of lower petals.*—2.1–2.5 cm.

*Petal shape.*—Obovate.

*Apex shape.*—Rounded.

*Margin.*—Entire.

*Petal texture.*—Papillose.

*Number of petaloids.*—2–3.

*Color of petaloids.*—Slightly lighter than RHS 45B.

*Duration of flowering.*—Continuous flowering throughout the Summer.

Bud (just before opening):

*Color.*—RHS 46B.

*Length.*—1.2–1.4 cm.

*Width.*—0.7–0.9 cm.

*Shape.*—Elliptical.

*Number of sepals.*—5, fused at the base.

*Color of sepals.*—RHS 144A; RHS 187B overlay basally.

*Length of sepals.*—1.1–1.4 cm.

*Width of sepals.*—0.3–0.4 cm.

*Sepal shape.*—Lanceolate.

*Apex shape.*—Acute.

*Margin.*—Entire.

*Texture.*—Pilose and slightly villous; glandular hairs.

Reproductive organs:

*Pistil.*—1.

*Length.*—0.8–0.9 cm.

*Style color.*—RHS 184A.

*Style length.*—0.3–0.4 cm.

*Stigma color.*—RHS 185A.

*Number of anthers.*—4–6.

*Color of filaments.*—RHS N155B but whiter; RHS 51A towards the anthers.

*Length of filaments.*—0.6–0.7 cm.

*Pollen amount.*—Moderate.

*Color of pollen.*—RHS N172A.

*Fertility/seed set.*—Not observed on this hybrid.

Disease/pest resistance: Disease resistance or susceptibility has not been observed on this hybrid.

What is claimed is:

1. A new and distinct variety of *Pelargonium* plant named 'Cope Scarfir,' substantially as illustrated and described herein.

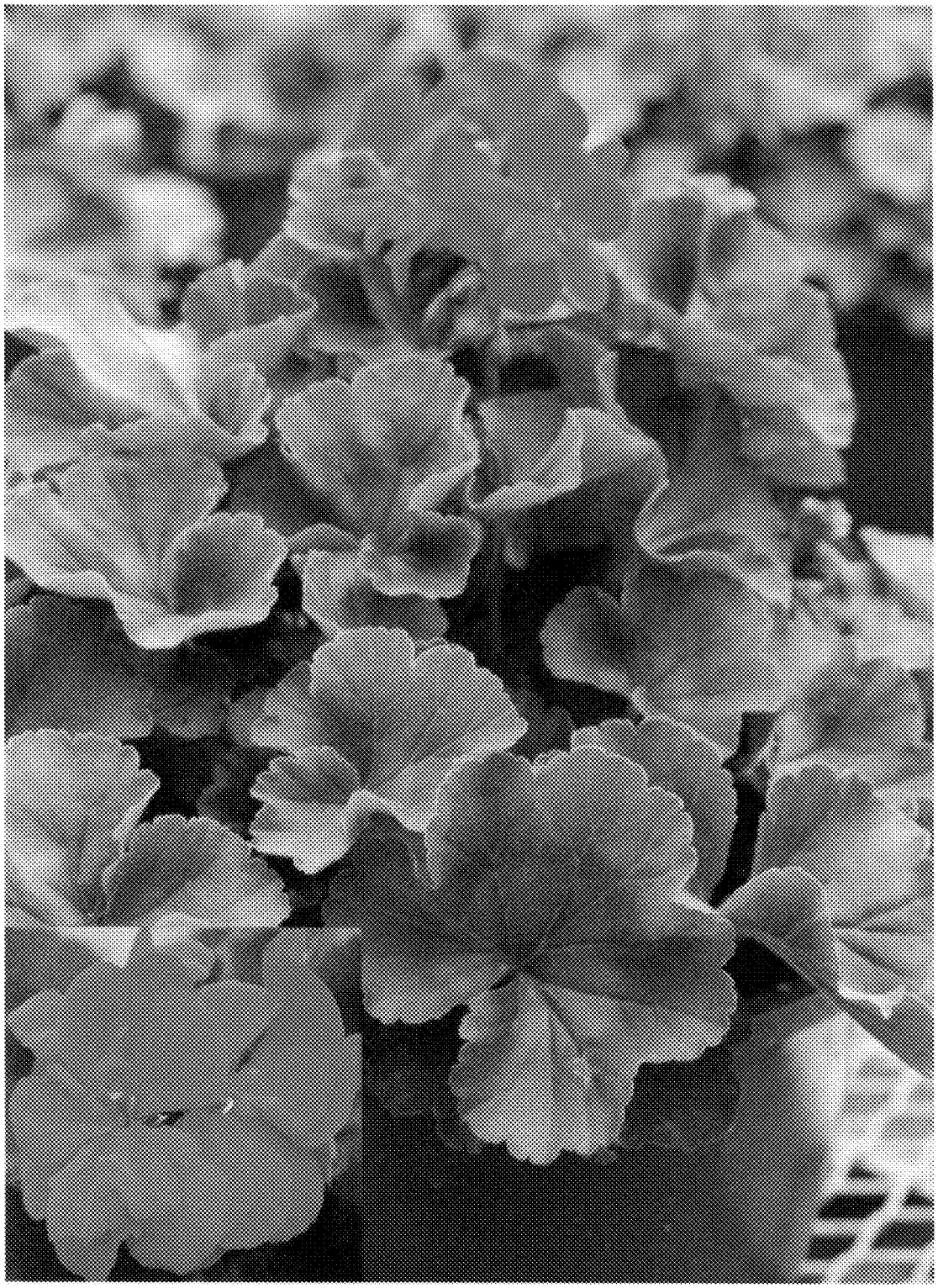

* * * * *